United States Patent [19]

Baysdon et al.

[11] Patent Number: 5,051,512

[45] Date of Patent: Sep. 24, 1991

[54] PROCESS FOR PREPARATION OF FLUOROMETHYL-SUBSTITUTED PIPERIDINE CARBODITHIOATES

[75] Inventors: Sherrol L. Baysdon, Chesterfield; Mitchell J. Pulwer, St. Louis; Helen L. Janoski, St. Peters, all of Mo.

[73] Assignee: Monsanto Company, St. Louis, Mo.

[21] Appl. No.: 495,172

[22] Filed: Mar. 19, 1990

[51] Int. Cl.$^5$ .......................................... C07D 211/40
[52] U.S. Cl. .................................. 546/243; 546/245; 558/253; 558/256
[58] Field of Search ............... 546/243, 245; 558/253, 558/256

[56] References Cited

U.S. PATENT DOCUMENTS

| | | | |
|---|---|---|---|
| 3,873,301 | 3/1975 | O'Brien et al. | 546/245 |
| 3,953,427 | 4/1976 | Matolcsy et al. | 546/245 |
| 4,618,679 | 10/1986 | Lee | 546/243 |
| 4,692,184 | 9/1987 | Lee | 71/94 |

Primary Examiner—C. Warren Ivy
Assistant Examiner—Ba K. Trinh
Attorney, Agent, or Firm—James C. Bolding; Stanley M. Tarter; Grace L. Bonner

[57] ABSTRACT

Described herein is a process for preparation of substituted piperidine dicarbothioate compounds.

3 Claims, No Drawings

PROCESS FOR PREPARATION OF FLUOROMETHYL-SUBSTITUTED PIPERIDINE CARBODITHIOATES

Methods for preparation of 2,6-bis(fluorinated methyl)-pyridine dicarboxylates and pyridine dicarbothioates are disclosed in U.S. Pat. Nos. 4,692,184 and 4,618,679 and in European Patent 135,491. These compounds are useful as herbicides.

The compound methyl 4,4,4-trifluoro-3-oxobutanethioate (sometimes referred to herein as thiomethyl trifluoroacetoacetate, or TMTFAA) is mentioned as a starting material in the preparation of such pyridine dicarbothioates in U.S. Pat. No. 4,785,129.

DESCRIPTION OF THE PRIOR ART

As used herein, the following terms have the following meanings:

Dithiopyr—2-difluoromethyl-4-(2-methylpropyl)-6-trifluoromethyl-3,5-dicarbothioic acid, S,S-dimethyl ester
DABCO—1,4 -diazabicyclo-[2.2.2]-octane
DBU—1,8-diazabicyclo-[5.4.0]-undec-7-ene
ETFAA—ethyl 4,4,4-trifluoro-3-oxo-butanoate
TMTFAA—methyl 4,4,4-trifluoro-3-oxo-butanethioate
IVA—isovaleraldehyde, or 3-methyl-butanal
NMR—nuclear magnetic resonance
GLC—gas-liquid chromatography
% Assay—Weight % desired product compound
% Yield—100×mols desired product / mol initial IVA starting material.
NOTE: Where a yield is shown herein in discussing the effect of varying a process parameter, all process variables not explicitly shown to be varied are held constant.

As outlined in Scheme I, preparation of diethyl 2-difluoromethyl-4-(2-methylpropyl)-6-trifluoromethyl-3,5-pyridine dicarbothioate is accomplished by a Hantzsch-type base catalyzed intermolecular cyclization of ethyl 4,4,4-trifluoro-3-oxo-butanoate (ethyl trifluoroacetoacetate, or ETFAA) and isovaleraldehyde to form a substituted dihydroxypyran, followed by ammonolysis. Dehydration of the resultant dihydroxypiperidines gives a mixture of 1,4 and 3,4 dihydropyridine isomers. Dehydrofluorination of the dihydropyridines using an organic base such as DBU or 2,6-lutidine affords good yields (80% overall) of the pyridine diethylester.

Saponification of the diester, conversion of the resulting diacid to the diacid chloride, and subsequent thioesterification yields the preferred pyridine dicarbothioate herbicide dithiopyr.

The seven-step procedure carried out according to the reaction conditions and using the solvents and reagents disclosed in the prior art affords yields of dithiopyr in the range of 60% based on the starting IVA.

By analogy to the process of Scheme I, one might reason that a process could be developed starting with TMTFAA rather than ETFAA which would provide the desired pyridine dicarbothioate directly in four reaction steps rather than seven while employing process conditions which are the same as, or similar to, those shown in the prior art teachings. However, in practice using the overall reaction sequence of Scheme II and proceding by way of the pyran as an intermediate using the solvents and reagents employed in the first four steps of Scheme I, a low yield of the desired pyridine dicarbothioate is obtained based on the starting TMTFAA. This is shown below in the Comparative Example.

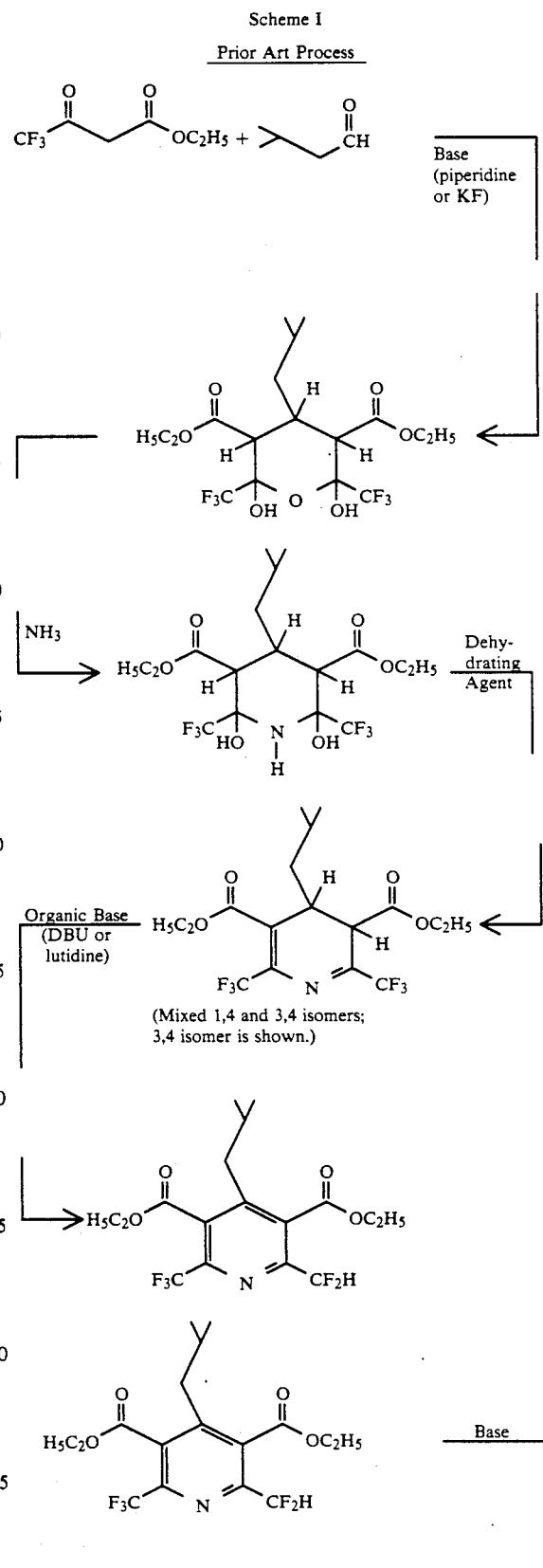

Scheme I

Prior Art Process

Scheme I

Prior Art Process

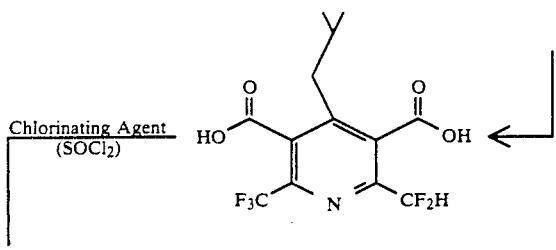

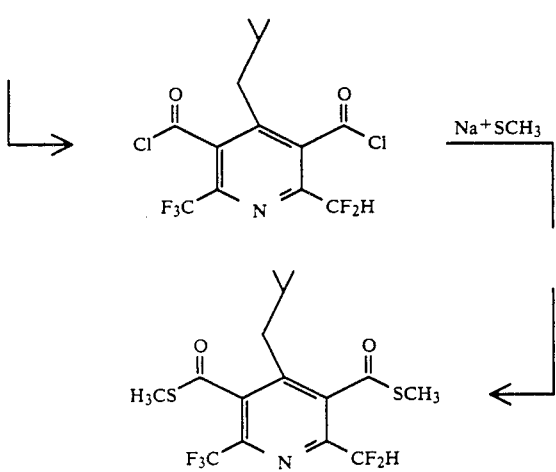

Scheme II

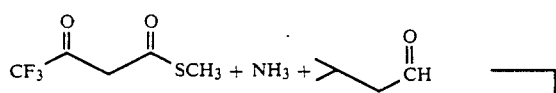

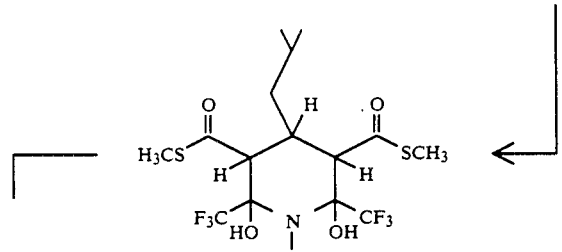

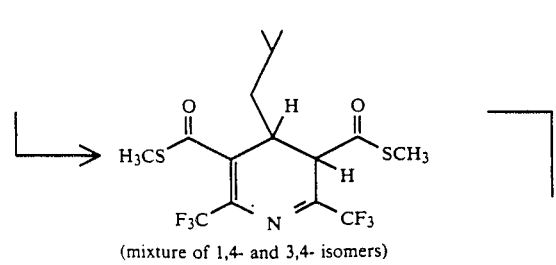

(mixture of 1,4- and 3,4- isomers)

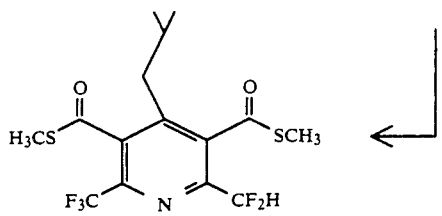

COMPARATIVE EXAMPLE

When TMTFAA (2 equivalents) and isovaleraldehyde (1 equivalent) were reacted in the presence of catalytic piperidine in toluene, an exotherm was observed. After stirring for 12 h at 25° C., $^{19}F$ NMR showed the presence of the pyrans.

When the pyran-forming reaction was substantially complete (after about 12 hours), NH$_3$ was bubbled into the toluene solution until it reached saturation. The resulting solution was stirred overnight at room temperature after which a $^{19}F$ NMR spectrum indicated the presence of cis and trans isomers of the dihydroxypiperidine.

The toluene solution of dihydroxypiperidines was treated with concentrated H$_2$SO$_4$ as a dehydrating agent at low temperature as described in U.S. Pat. No. 3,692,184 to form a mixture of dihydropyridine isomers. The reaction mixture was stirred an additional 2 h and then poured onto ice. After drying, the toluene solution was treated with tributylamine at reflux to dehydrofluorinate the dihydropyridines, affording the desired product dithiopyr. The presence of this desired product was confirmed by analysis, but the yield was very low (less than 20% by weight).

DESCRIPTION OF THE INVENTION

As in the Comparative Example above, the process of this invention is illustrated in detail below with reference to the preparation of specific pyridine dicarbothioate compounds.

To improve yield of the desired pyridine dicarbothioate product, the following process of the present invention generally employs the same reaction steps as Scheme II but minimizes solvent changes between steps and employs reagents which are more suited to the thioester compounds encountered as starting materials and products in the various steps. Moreover, process efficiency and economics are improved in the present process through the use in some instances of reagents which need not be recovered.

The overall process outlined above for the preparation of the desired pyridine dicarbothioate product from TMTFAA consists of three operations which can be carried out in a single reaction vessel without isolation of intermediate compounds. These three operations are piperidine formation, dehydration, and dehydrofluorination, and each of these is described in detail below.

PIPERIDINE FORMATION

The initial operation in this process consists of a Hantzsch-type cyclization reaction which is performed preferably in a solvent which is a lower alkylnitrile. Acetonitrile and butyronitrile are particularly preferred. In this reaction which combines Steps 1 and 2 of Scheme I into Step 1 of Scheme II, two molecules of TMTFAA, a molecule of IVA (isovaleraldehyde), and a molecule of ammonia combine to afford the intermediate dihydroxypiperidines. The source of the ammonia ($NH_3$) in this reaction step may be anhydrous ammonia or an ammonium salt (including ammonium hydroxide) which will readily yield ammonia; ammonium hydroxide is less desirable because its use entails addition of water to the process, and the water thus added must be removed prior to the dehydration step which follows.

When $NH_3$ is used it may optionally be added to a small portion of the total TMTFAA to form an ammonium salt of TMTFAA, and this salt may be added to the balance of the TMTFAA and the IVA. It is believed that this ammonium salt of TMTFAA is formed in the process as described herein in any event, but this technique may provide certain advantages in handling the process reagents. The salt has the formula

and may be isolated.

The IVA generally is the limiting reagent in this reaction, whereas in the prior art generally the trifluoroacetoacetate ester is the limiting reagent. The most preferred method of carrying out this operation in terms of cost vs. yield is the one which uses substantially stoichiometric amounts of each of the reagents. In a particularly preferred embodiment of this process, acetonitrile or butyronitrile is charged to the reaction vessel in an amount by weight equal to the total weight of the reactants along with the desired amount of TMTFAA. Gaseous ammonia ($NH_3$) is then added subsurface at a temperature below 20° C. The desired amount of isovaleraldehyde is then added dropwise while maintaining the temperature of the reaction mixture below 20° C. The reaction is allowed to warm to 25° C. and then heated for 4 hours at 65° C. After completion of the above reaction sequence, volatiles are removed in vacuo at 50°-60° C. and 10 torr in preparation for the dehydration reaction. In this first operation just described, it should be noted that the order of addition of reactants, the temperature, and the catalyst are different from those of the prior art: specifically, the TMTFAA is treated with ammonia either prior to addition of the aldehyde or in the presence of the aldehyde prior to reaction of the TMTFAA and the IVA to form a pyran, at a temperature below about 30° C. and preferably below about 20° C., and without addition of piperidine as a catalyst according to the teaching of the prior art.

The effect of some of the process parameters in this step on the overall yield is shown in the following Table. In all of these runs the solvent used was acetonitrile and ammonia addition was carried out below 20° C.

TABLE

| Run | ratio TMTFAA to IVA | method of ammonia addition | Temp (°C.) | Time (h) | Yield (%) |
|---|---|---|---|---|---|
| 1 | 3/1 | $NH_3$ added to TMTFAA, followed by IVA | 50 | 5 | 71 |
| 2 | 2/1 | $NH_3$ added to TMTFAA, followed by IVA | 50 | 5 | 64 |
| 3 | 3/1 | Ammonium acetate added to TMTFAA, followed by IVA | 60 | 3 | 67 |
| 4 | 2/1 | $NH_3$ added to mix of TMTFAA and IVA | 65 | 4 | 64 |
| 5 | 2/1.2 | $NH_3$ added to mix of TMTFAA and IVA | 65 | 4 | 60 |
| 6 | 2/1 | $NH_3$ added to TMTFAA to form a salt; salt added to mix of TMTFAA and IVA | 50 | 4.5 | 62 |

DEHYDRATION

The second operation of this process corresponds to Step 2 of Scheme II and involves dehydration of the dihydroxypiperidines produced in the first step of the process. In this step two molecules of $H_2O$ are removed from the piperidines to afford a mixture of dihydropyridine isomers. In practice this is accomplished by treating the crude dihydroxypiperidine residue from Step 1, either neat or in a solution, with a dehydrating agent. It is preferred to perform the dehydration on the neat piperidine product (i.e., in the absence of a solvent) using anhydrous or concentrated aqueous HCl. In a particularly preferred aspect of this process, the crude dihydroxypiperidine residue from the first step is mixed with 32% aqueous HCl in a ratio of about 5 to about 15 mols HCl per mol of IVA used in the first step and heated to 80° C. for 1-2 hours. The mixture is cooled to 40° C., and an amount of toluene equal in weight to the initial acetonitrile charge is added. The toluene/HCl mixture is stirred for 30 minutes, after which agitation is stopped and the two phases are allowed to separate. The lower aqueous acid layer is removed. A sufficient amount of aqueous base is added to the toluene solution to obtain a stable pH in the range 8-10. Additional runs showing the effect of the dehydration reaction temperature, HCl concentration, dehydration reaction time and molar ratio of HCl to IVA used in the first step on product yield are shown in the following Table. All runs in this Table were performed without using an organic solvent in this step.

| RUN | TEMP (°C.) | HCl CONC (%) | REACTION TIME (h) | MOL RATIO (HCl/IVA) | FINAL PRODUCT YIELD (%) |
|---|---|---|---|---|---|
| 1 | 70 | 35 | 3 | 10 | 62 |
| 2 | 60 | *Anhy | 3 | 15 | 52 |
| 3 | 70 | 20 | 5 | 10 | 48 |
| 4 | 50 | 35 | 4 | 10 | 17 |
| 5 | 60 | 35 | 3 | 10 | 62 |
| 6 | 70 | 32 | 3 | 5 | 46 |
| 7 | 70 | 32 | 2 | 10 | 52 |
| 8 | 65 | 32 | 4 | 10 | 64 |
| 9 | 80 | 32 | 2 | 10 | 62 |

*Anhy means "anhydrous".

In an alternative embodiment of this dehydration step in which a solvent is used, the preferred combination of solvent and dehydrating agent is acetic acid with $PCl_3$.

It has now quite unexpectedly been found that when the novel dehydration process herein is employed using either HCl to treat the neat starting material or when $PCl_3$ is used with acetic acid as a solvent a novel compound is produced in substantial quantities. This new compound is 3,5-pyridinedicarbothioic acid, 2-chloro- 1,2,3,4-tetrahydro-4-(2-methylpropyl)-2,6-bis(trifluoromethyl)-, S,S-dimethyl ester, Mp 154°-155° C.

The above-described dehydration of dihydroxypiperidine thioesters using HCl as the dehydrating agent applies also to the dehydration of the corresponding oxyesters such as those of Scheme 1. The use of HCl as the dehydrating agent for the oxyesters results in significant operational advantages as compared to the sulfuric acid dehydration method for oxyesters according to the prior art teachings.

DEHYDROFLUORINATION

According to the present invention, the final step of the process of Scheme II, dehydrofluorination of the dihydropyridines prepared in the previous step to afford the final pyridine dicarbothioate product, is accomplished by treatment with DABCO in contrast to the prior art dehydrofluorination step which employs DBU or 2,6-lutidine as the organic base.

In this process step, DABCO may be employed in either stoichiometric or catalytic amounts. Because DABCO is a difunctional base, the stoichiometric DABCO method uses at least one half mol of DABCO per mol of starting IVA. Use of about one mol of DABCO is preferred. The catalytic DABCO method, on the other hand, employs substantially less DABCO such as about 0.01 to 0.50, and preferably about 0.05 to about 0.20 mol DABCO per theoretical mol of dihydropyridines (i.e., per mol of original IVA) in conjunction with an amount of an additional base which is adequate to effect substantially complete dehydrofluorination. The additional base used in the process in which DABCO is employed as a catalyst is a base selected from yhe group consisting of $K_2CO_3$, $K_2CO_3$, triethylamine, and tributylamine. Use of a catalytic amount of DABCO thus may result in a substantial economic benefit in the process.

Whichever dehydrofluorination method is employed, it is desirable to have some water present in the process to act as a solvent for salts (such as, for example, the hydrofluoride salt of DABCO and/or of the additional base if one is used) which may be formed in the process.

Using DABCO in either the catalytic or stoichiometric amounts, the new compound 3,5-pyridinedicarbothioic acid, 2-chloro-1,2,3,4-tetrahydro-4-(2-methylpropyl)-2,6-bis(trifluoromethyl)-, S,S-dimethyl ester is dehydrohalogenated to dithiopyr via the loss of HCl and HF from the molecule.

Whichever specific dehydrofluorination method is used, it is desirable to conduct this process step in the presence of an inert aprotic solvent. Such solvents include, but are not limited to, benzene, toluene, xylenes, cyclohexane, monochlorobenzene, butyronitrile, and like solvents. Moreover, while the temperature used in this process step is not particularly critical, it is preferred to use temperatures in the range of 50° C. to 120° C., preferably 60° C. to 80° C.

In a particularly preferred embodiment using the catalytic DABCO dehydrofluorination method, the toluene solution from Step 2 is sparged vigorously with nitrogen to minimize formation of oxidation by-products. An aqueous solution of 40% $K_2CO_3$ containing 0.6 to 1.0 mol $K_2CO_3$ per theoretical mol of dihydropyridine (or per mol/original mol IVA) is likewise degassed with nitrogen. The two solutions are combined and a catalytic amount (5 to 20 mol % based on mols of original IVA charge) of DABCO is added as a solid. The resulting blood red solution is heated at between about 60° and 100° C. for about 4 hours, cooled, and the aqueous layer is removed. The toluene layer is stripped in vacuo to afford the crude pyridine dicarbothioate in 65-70% overall yield based on the initial amount of IVA charged with a wt% assay in the range of 80-85%.

Using the stoichiometric DABCO dehydrofluorination method, the toluene solution from Step 2 is sparged vigorously with nitrogen to minimize oxidation by-products. DABCO in an aqueous solution preferably at or near saturation in a ratio greater than 0.50 mol, and preferably about 1 mol per theoretical mol of dihydropyridine (or 1 mol/original mol IVA) is likewise sparged with nitrogen, and the two solutions are combined. The resulting blood red solution is heated to 70° C. for about 2 hours, cooled, and the aqueous layer drained. The toluene layer is washed with two portions of 1N HCl to remove residual DABCO, then stripped in vacuo to afford the crude pyridine dicarbothioate in 6-70% overall yield based on the initial amount of TMTFAA charged with a wt% assay in the range of 80-85%.

The following Examples 1 and 2 illustrate the process of this invention as it is used to prepare the same specific pyridine dicarbothioate compound dithiopyr shown in the Comparative Example presented earlier.

EXAMPLE 1

The following Example 1 illustrates the use of a catalytic amount of DABCO in the dehydrofluorination step and concentrated HCl in the dehydration step.

A reaction flask is charged with TMTFAA (0.025 mols, 5 g) and 15 g acetonitrile and cooled to 10 C. Ammonia (0.43 g, 0.025 mols) is sparged subsurface to the acetonitrile/TMTFAA solution while the temperature is maintained below 20 C. Following the ammonia addition, a mixture of TMTFAA (0.025 mols, 5 g) and IVA (0.025 mols, 2.19 g) is added dropwise to the flask while continuing to maintain the temperature below 20C. After this addition the reaction mixture is stirred 30 minutes at 20 C or less and then heated to 65 C for 4 hours. When the reaction is complete the pressure in the reactor is slowly reduced to 10 torr to remove the acetonitrile solvent, and when the solvent has been completely removed the reactor pressure is increased to atmospheric with nitrogen. To the stripped step 1 product is added 32% HCl (29 g, 0.25 mols), and the mixture is heated to 80 C for 2 hours. Toluene (15 g) is added to the reactor, the reaction is cooled to 30 C, and the phases are allowed to separate for 1 hour. Following removal of the lower aqueous layer, the pH of the toluene solution is adjusted with 30% $K_2CO_3$ to within a range of 8-9. A charge of 30% $K_2CO_3$ (11.36g, 0.025 mols) and DABCO (0.14 g, 0.0013 mols) is added to the reactor, which is then heated to reflux (85° C.) for 4 hours. When the reaction is complete, the contents are cooled to 30° C. and the phases allowed to separate. Following removal of the lower aqueous layer, the toluene solvent was removed under vacuum to obtain 7.73 g of crude product with an assay of 79% of the desired compound. The overall process yield of the pyridine carbodithioate was 61%.

The effect of the solvent used in this step is shown in the following Table, in which in each run the temperature was held at 85° C., the time was 4 hours, the catalytic amount of DABCO was 6% of the initial molar amount of IVA, and the molar ratio of $K_2CO_3$ to initial IVA was 1.0.

| Run | Solvent | Yield |
|---|---|---|
| 1 | Toluene | 64% |
| 2 | Monochlorobenzene | 61% |
| 3 | Butyronitrile | 48% |

EXAMPLE 2

The following Example 2 shows the use of a stoichiometric amount of DABCO for dehydrofluorination and POCl$_3$ for dehydration.

TMTFAA (0.025 mols, 5 g) and 15 g acetonitrile are charged to a flask and cooled to 10° C. Ammonia (0.43g, 0.025 mols) is sparged subsurface into the solution while the temperature is maintained below 20° C. Following this NH$_3$ addition, a mixture of TMTFAA (0.025 mols) and IVA (0.025 mols, 2.19 g) is added dropwise to the acetonitrile solution, again maintaining the temperature below 20° C. The mixture is stirred for 30 minutes at 25° C. or below, then heated to 65° C. for 4 hours to complete the reaction. Acetonitrile solvent is removed by reducing reactor pressure slowly to 10 torr and maintaining a temperature of 65° C. The reactor is returned to atmospheric pressure under a N$_2$ blanket, and 15 g of toluene is added followed by POCl$_3$ (0.03 mols). The reaction flask is heated to 70° C. and held for 1 hour then cooled to below 30° C. Water is added slowly in an amount equal in weight to the toluene charge (15 g), maintaining the 30° C. temperature. The water layer is separated and removed, then the pH of the toluene solution is adjusted with 20% NaOH to within the range of 8-9, after which the aqueous layer is removed. DABCO (0.025 mols, 2.8 g) and 2.8 g water are combined, sparged with nitrogen, and added to the toluene solution which has been sparged with nitrogen. The mixture is heated to 70° C. for 2 hours, then cooled to 25°-30° C. and the aqueous layer was removed. The organic layer is washed with two portions of 1N HCl (20 g), separated and dried over MgSO$_4$. The toluene is removed under vacuum to afford crude product dithiopyr. The overall yield of dithiopyr in this example is 66%.

While the process of this invention has been specifically illustrated in terms of a specific pyridine dicarbothioate product, it is equally applicable to the preparation of other pyridine compounds. Selection of the aldehyde starting material will, of course, determine the substituent at the 4-position of the final pyridine product. Likewise it is evident that lower alkyl trifluoroacetoacetate thioesters other than the methylthio ester may equally well be employed. Accordingly, the scope of this invention is to be limited only in accordance with the annexed claims.

We claim:

1. A process for preparing 4-(lower alkyl)-2,6-bis(trifluoromethyl)-2,6-dihydroxy-3,5-piperidinedicarbothioic acid, S,S-dimethyl ester comprising the steps of:
    a) bringing into reactive contact at a temperature below about 30° C. in a lower alkylnitrile solvent trifluoroacetoacetate acid thiomethyl ester and ammonia to form the ammonium compound having the structural formula

b) thereafter bringing the reaction mixture of step (a) into reactive contact at a temperature below about 30° C. with a lower alkyl aldehyde; and
    c) heating the reaction mixture of step (b) to produce 4-(lower alkyl)-2,6-bis(trifluoromethyl)-2,6-dihydroxy-3,5-piperidinedicarbothioic acid, S,S-dimethyl ester.

2. The process of claim 1, wherein the lower alkyl aldehyde is isovaleraldehyde.

3. The process of claim 1, wherein the solvent is acetonitrile or butyronitrile.

* * * * *

UNITED STATES PATENT AND TRADEMARK OFFICE
CERTIFICATE OF CORRECTION

PATENT NO. : 5,051,512
DATED : September 24, 1991
INVENTOR(S) : S. L. Baysdon et al.

It is certified that error appears in the above-identified patent and that said Letters Patent is hereby corrected as shown below:

| Col. | Line |  |
|---|---|---|
| 5 | 21 | Remove |

"  "

and insert

-- 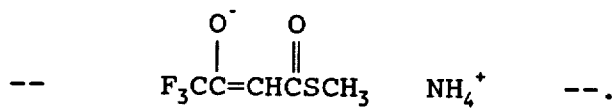 --.

| 10 | 21 | Remove "trifluoroacetoacetate" and insert -- trifluoroacetoacetic --. |

UNITED STATES PATENT AND TRADEMARK OFFICE
CERTIFICATE OF CORRECTION

PATENT NO. : 5,051,521
DATED : September 24, 1991
INVENTOR(S) : S. L. Baysdon et al.

It is certified that error appears in the above-identified patent and that said Letters Patent is hereby corrected as shown below:

Col. Line 10   25   Remove

"      "

and insert

--   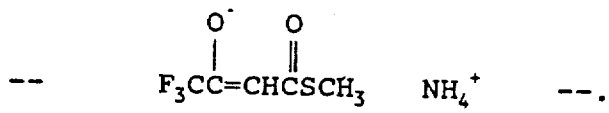   --.

Signed and Sealed this

Second Day of February, 1993

Attest:

STEPHEN G. KUNIN

Attesting Officer    Acting Commissioner of Patents and Trademarks